(12) United States Patent
Shim et al.

(10) Patent No.: US 9,439,764 B2
(45) Date of Patent: Sep. 13, 2016

(54) MEMBRANE-TYPE ARTIFICIAL SCAFFOLD AND METHOD FOR FABRICATING SAME

(71) Applicant: POSTECH ACADEMY-INDUSTRY FOUNDATION, Pohang-si (KR)

(72) Inventors: Jin-Hyung Shim, Pohang-si (KR); Dong-Woo Cho, Seoul (KR); Jeoung Yong Kim, Seoul (KR); Jong Young Kim, Daegu (KR)

(73) Assignee: POSTECH ACADEMY-INDUSTRY FOUNDATION, Pohang-Si (KR)

( * ) Notice: Subject to any disclaimer, the term of this patent is extended or adjusted under 35 U.S.C. 154(b) by 148 days.

(21) Appl. No.: 14/349,514

(22) PCT Filed: Oct. 17, 2012

(86) PCT No.: PCT/KR2012/008488
§ 371 (c)(1),
(2) Date: Apr. 3, 2014

(87) PCT Pub. No.: WO2013/058547
PCT Pub. Date: Apr. 25, 2013

(65) Prior Publication Data
US 2014/0296996 A1    Oct. 2, 2014

(30) Foreign Application Priority Data

Oct. 18, 2011  (KR) .................. 10-2011-0106420

(51) Int. Cl.
*A61F 2/28*       (2006.01)
*A61L 27/18*      (2006.01)
(Continued)

(52) U.S. Cl.
CPC ............... *A61F 2/28* (2013.01); *A61F 2/2846* (2013.01); *A61L 27/18* (2013.01); *A61L 27/32* (2013.01);
(Continued)

(58) Field of Classification Search
CPC ...... A61F 2/28; A61F 2/2846; A61F 2/3094; A61L 27/18
See application file for complete search history.

(56) References Cited

U.S. PATENT DOCUMENTS

2010/0137491 A1* 6/2010 Rose .................. A61L 31/128
                                                     524/417
2010/0196432 A1* 8/2010 Feinberg ............. A61L 27/3804
                                                     424/422
(Continued)

FOREIGN PATENT DOCUMENTS

CN      1887365      1/2007
CN      102166378    8/2011
(Continued)

OTHER PUBLICATIONS

Chinese Search Report(Attached to the Office Action dated Jan. 26, 2015), Application No. 2012800510107, Jan. 14, 2015.
(Continued)

*Primary Examiner* — Jason-Dennis Stewart
(74) *Attorney, Agent, or Firm* — Lex IP Meister, PLLC

(57) ABSTRACT

Provided herein are a membrane-type artificial scaffold for guided bone regeneration (GBR) and a method for fabricating the same. The membrane-type artificial scaffold according to the present invention comprises: a first layer made of at least one fiber layer arranged in parallel with each other with a first spacing therebetween such that the fiber layer contacts a bone tissue in vivo; and a second layer stacked on the first layer and made of at least one fiber layer arranged parallel to each other with a second spacing therebetween such that the fiber layer contacts a soft tissue in vivo. The first spacing is larger than the second spacing.

12 Claims, 9 Drawing Sheets

(51) Int. Cl.
*A61L 27/32* (2006.01)
*A61L 27/56* (2006.01)
*A61L 27/58* (2006.01)
*B32B 5/12* (2006.01)
*B32B 5/26* (2006.01)
*A61F 2/30* (2006.01)

(52) U.S. Cl.
CPC .............. *A61L 27/56* (2013.01); *A61L 27/58* (2013.01); *B32B 5/12* (2013.01); *B32B 5/26* (2013.01); *A61F 2/3094* (2013.01); *A61F 2002/30009* (2013.01); *A61F 2002/30914* (2013.01); *A61L 2430/02* (2013.01); *B32B 2250/20* (2013.01); *B32B 2255/02* (2013.01); *B32B 2255/26* (2013.01); *B32B 2262/0276* (2013.01); *B32B 2307/728* (2013.01)

(56) References Cited

U.S. PATENT DOCUMENTS

| | | | | |
|---|---|---|---|---|
| 2010/0318108 | A1* | 12/2010 | Datta | A61L 31/10 606/151 |
| 2011/0060413 | A1 | 3/2011 | Kasuga | |
| 2011/0144763 | A1* | 6/2011 | Bagga | A61L 27/427 623/23.61 |
| 2014/0128991 | A1* | 5/2014 | Atanasoska | A61L 27/14 623/23.72 |

FOREIGN PATENT DOCUMENTS

| | | |
|---|---|---|
| EP | 2548588 | 1/2013 |
| JP | 2004-141301 | 5/2004 |
| JP | 2004-298544 | 10/2004 |
| JP | 2007-510509 | 4/2007 |
| JP | 2008-307180 | 12/2008 |
| JP | 2011-212209 | 10/2011 |
| KR | 10-2010-0013016 | 2/2010 |
| KR | 10-2011-0025327 | 3/2011 |
| KR | 10-1067827 | 9/2011 |
| WO | 2005/018698 | 3/2005 |
| WO | 2008/041563 | 4/2008 |
| WO | 2011/059746 | 5/2011 |
| WO | 2011/115381 | 9/2011 |

OTHER PUBLICATIONS

Jong Young Kim, et al., "Fabrication of blended PCL/HA scaffold via multi-head deposition system" page, Transactions of the Korean Society of Mechanical Engineers, 2010 Fall Symposium, 4015-4016 (Nov. 2010).

R K Schenk et al., "Healing pattern of bone regeneration in membrane-protected defects: a histologic study in the canine mandible", The International journal of oral & maxillofacial implants, Jan. 1, 1994, pp. 1-35, XP055187954.

The extended European Search Report, May 18, 2015, European Patent Application No. 12842060.1.

* cited by examiner

МЕMBRANE-TYPE ARTIFICIAL SCAFFOLD AND METHOD FOR FABRICATING SAME

FIELD OF THE INVENTION

The present invention relates to a membrane type scaffold, and more particularly, to a membrane type scaffold for guided bone regeneration (GBR), and a method of manufacturing the same.

DESCRIPTION OF THE RELATED ART

Tissue engineering is a technology field in which cells collected in a small quantity from tissue of a patient in order to regenerate a damaged organ are cultured in a large quantity and then differentiated into three dimensional tissue to regenerate tissue and organs therefrom. A scaffold which allows the cells to be recognized in a three dimensional environment is required to perform three dimensional cultivation of tissue.

Examples of a method of regenerating a damaged lower jawbone in a dental field include guided bone regeneration (GBR). In this curing method, a role of a membrane type scaffold is very important. The membrane type scaffold mainly serves to surround a damaged portion of the bone, prevent soft tissue such as gum tissue from permeating the damaged portion of the bone, and guide regeneration of bone tissue again.

Currently, a non-water absorbent material of an ePTFE (expanded polytetrafluoroethylene) or titanium material is used as a commercially available membrane type scaffold. The scaffold has excellent mechanical strength and biocompatibility, but when the scaffold is implanted in the body, since the scaffold is stacked as fiber tissue, in the case where the scaffold is used in bone tissue, the scaffold causes a problem when combined with peripheral bones.

Further, an existing membrane type scaffold has a structure that does not include a void or it is difficult to easily control a size of the void, and there are many cases where the scaffold has a sponge shape in which an internal structure type is heterogeneous. Since the structure that does not include a void is not properly fused with bone tissue, there is a stripping problem, and the sponge structure has a problem in that since mechanical strength is weak, the scaffold does not have a space maintenance ability that should be basically equipped in the scaffold.

The above information disclosed in this Background section is only for enhancement of understanding of the background of the invention and therefore it may contain information that does not form the prior art that is already known in this country to a person of ordinary skill in the art.

DESCRIPTION OF THE INVENTION

Technical Object

The present invention has been made in an effort to provide a membrane type scaffold that is not stripped after an operation by using a material having high affinity to peripheral tissue and can improve mechanical strength and a space maintenance ability by forming a void having a regular shape.

Further, the present invention has been made in an effort to provide a method of manufacturing a membrane type scaffold, in which a size of the void can be easily adjusted and stripping between layers can be prevented.

Technical Solution

An exemplary embodiment of the present invention provides a membrane type scaffold including: a first layer disposed to come into contact with bone tissue in a body and including at least one fiber layer arranged in parallel at first intervals; and a second layer laminated on the first layer, disposed to come into contact with soft tissue in the body, and including at least one fiber layer arranged in parallel at second intervals, in which the first interval is larger than the second interval.

The first layer may include first fibers arranged in parallel at the first intervals and extending in a first direction, and the second layer may include second fibers arranged in parallel at the second intervals and extending in a second direction crossing the first direction.

The first interval may be in a range of 150 μm to 400 μm, and the second interval may be in a range of 30 μm to 50 μm. Heights of the first fibers and the second fibers may each be in a range of 50 μm to 100 μm.

The first fibers and the second fibers may include polycaprolactone (PCL), and the first fibers may further include at least one of hydroxyapatite and tricalcium phosphate (TCP).

The first fibers and the second fibers may further include at least one of polylactic acid (PLA), polyglycolic acid (PGA), and polylactic-co-glycolic acid (PLGA) as an accessory component in addition to polycaprolactone (PCL).

On the other hand, the first layer may include third fibers arranged at the first intervals and extending in a third direction, and fourth fibers fixed onto the third fibers, arranged at the first intervals, and extending in a fourth direction crossing the third direction. The second layer may include fifth fibers arranged at the second intervals and extending in a fifth direction, and sixth fibers fixed onto the fifth fibers, arranged at the second intervals, and extending in a sixth direction crossing the fifth direction.

The first interval may be in a range of 150 μm to 400 μm, and the second interval may be in a range of 30 μm to 50 μm. Heights of the third fibers, the fourth fibers, the fifth fibers, and the sixth fibers may each be in a range of 50 μm to 100 μm.

The third fibers, the fourth fibers, the fifth fibers, and the sixth fibers may include polycaprolactone (PCL), and the third fibers and the fourth fibers may further include at least one of hydroxyapatite and tricalcium phosphate (TCP).

The third fibers, the fourth fibers, the fifth fibers, and the sixth fibers may further include at least one of polylactic acid (PLA), polyglycolic acid (PGA), and polylactic-co-glycolic acid (PLGA) as an accessory component in addition to polycaprolactone (PCL).

Another exemplary embodiment of the present invention provides a method of manufacturing a membrane type scaffold, including: providing a first biopolymer and a second biopolymer to syringes of a first deposition head and a second deposition head, respectively; spraying the first biopolymer through a nozzle of the first deposition head to form a first layer including at least one fiber layer arranged in parallel at first intervals; and spraying the second biopolymer through a nozzle of the second deposition head on the first layer to form a second layer including at least one fiber layer arranged in parallel at second intervals, in which the first interval and the second interval have different values.

The first layer may be disposed to come into contact with bone tissue in a body, the second layer may be disposed to come into contact with soft tissue in the body, and the first interval may be larger than the second interval.

The first interval may be in a range of 150 μm to 400 μm, and the second interval may be in a range of 30 μm to 50 μm. A height of at least one fiber layer may be in a range of 50 μm to 100 μm.

The first layer and the second layer may include polycaprolactone (PCL), and the first layer may further include at least one of hydroxyapatite and tricalcium phosphate (TCP). The first layer and the second layer may further include at least one of polylactic acid (PLA), polyglycolic acid (PGA), and polylactic-co-glycolic acid (PLGA) as an accessory component in addition to polycaprolactone (PCL).

Technical Effects

In the membrane type scaffold of the present exemplary embodiment, it is possible to smoothly fuse bone tissue and the scaffold and prevent soft tissue from permeating a damaged portion of bone tissue simultaneously. Further, in the membrane type scaffold of the present exemplary embodiment, it is possible to increase mechanical strength and a space maintenance ability and easily adjust a size of a void when the membrane type scaffold is manufactured by forming the void having a regular shape.

DETAILED DESCRIPTION OF THE EMBODIMENTS

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
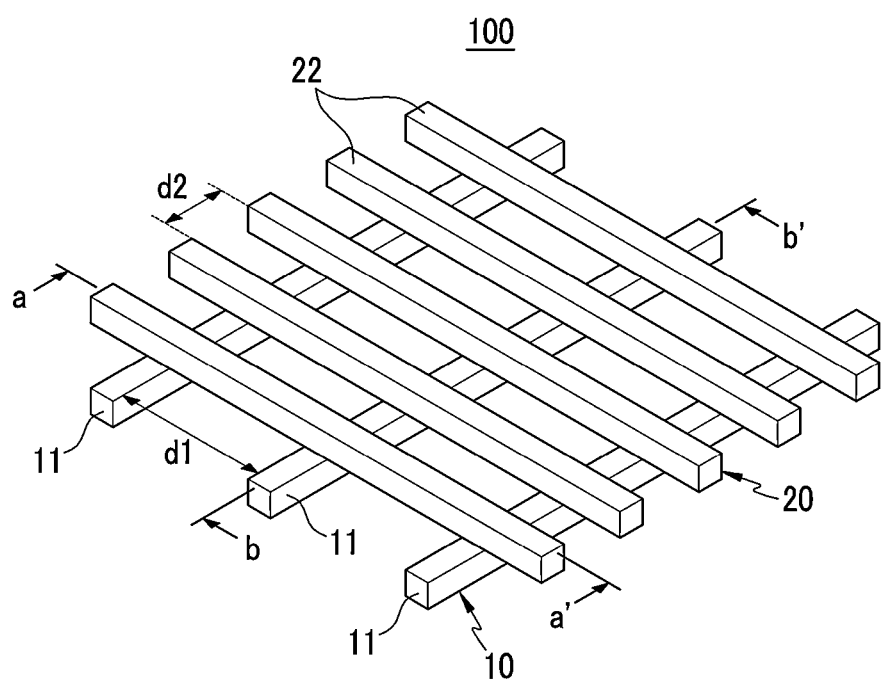
FIG. 1 is a schematic perspective view of a membrane type scaffold according to a first exemplary embodiment of the present invention.
Figure 2:
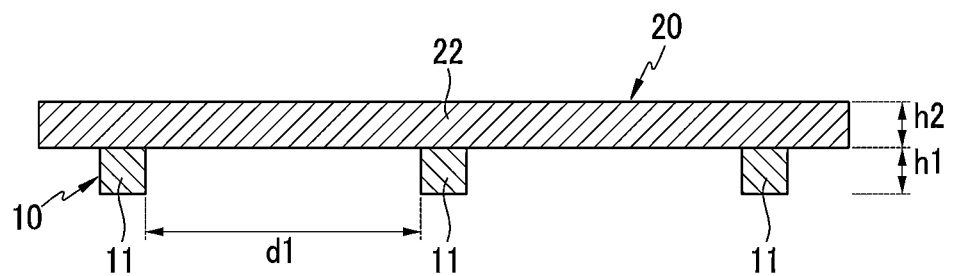
FIG. 2 is a cross-sectional view of the membrane type scaffold illustrated in FIG. 1, which is taken along line a-a'.
Figure 3:
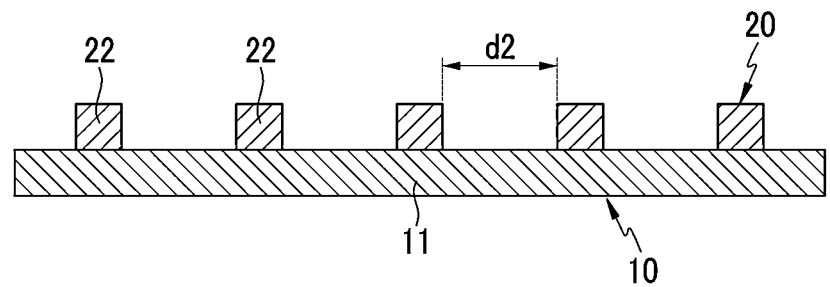
FIG. 3 is a cross-sectional view of the membrane type scaffold illustrated in FIG. 1, which is taken along line b-b'.

FIG. 1 is a schematic perspective view of a membrane type scaffold (hereinafter, referred to as 'scaffold') according to a first exemplary embodiment of the present invention, and FIGS. 2 and 3 are cross-sectional views of the scaffold illustrated in FIG. 1, which are taken along lines a-a' and b-b', respectively.

A scaffold 100 of the first exemplary embodiment is a scaffold positioned between hard tissue and soft tissue among various portions in the body, and may be used for guided bone regeneration of hard tissue. For example, the scaffold 100 is implanted to surround a damaged portion of a bone, and positioned between bone tissue that is hard tissue and gum tissue that is soft tissue.

Referring to FIGS. 1 to 3, the scaffold 100 of the first exemplary embodiment has a laminate structure of a first layer 10 coming into contact with bone tissue to constitute a bone tissue-affinitive layer and a second layer 20 coming into contact with soft tissue to constitute a soft tissue-affinitive layer. The first layer 10 and the second layer 20 form voids having different sizes according to a characteristic of contact tissue to increase biocompatibility.

Further, the entire scaffold 100 forms the voids having a regular shape to improve mechanical strength and a space maintenance ability. The scaffold 100 serves to prevent soft tissue from permeating a damaged portion of bone tissue, and help to regenerate new bone tissue from damaged bone tissue.

Specifically, the first layer 10 includes first fibers 11 arranged in parallel at first intervals d1 and extending in a first direction. In addition, the second layer 20 includes second fibers 22 arranged in parallel at second intervals d2 and extending in a second direction crossing the first direction. The second fibers 22 are fixed onto the first fibers 11.

The second direction may or may not be orthogonal to the first direction. FIG. 1 illustrates the case where the first direction and the second direction are orthogonal to each other as an example, but the second direction may cross the first direction at various angles.

Further, the first fibers 11 and the second fibers 22 may have various cross-sectional shapes such as a quadrangle, a circle, and an oval. FIGS. 1 to 3 illustrate the first fibers 11 and the second fibers 22 having a quadrangle cross-sectional shape as an example, but the cross-sectional shapes of the first and second fibers 11 and 12 can be variously modified.

In the first layer 10 coming into contact with bone tissue, the first interval d1 between the first fibers 11 may be in a range of 150 μm to 400 μm. This interval is a size that is advantageous to regenerate bone tissue, and when the interval satisfies this range, bone tissue and the scaffold may be smoothly fused. In this case, the first intervals d1 existing in the first layer 10 may have an error within ±20 μm.

Specifically, it is very important to set sizes of the first intervals d1 of the first layer 10 in proliferation and differentiation after a bone cell is disseminated in the scaffold 100. If the first interval d1 is less than 150 μm, a diffusion operation of oxygen or nutrients essential in survival of the bone cell is not performed well in the first layer 10, and vascular permeation essential in a procedure of regenerating bone tissue may not be easily performed thereinto. On the other hand, if the first interval d1 is more than 400 μm, total mechanical strength of the first layer 10 and the scaffold 100 is reduced, and protein synthesis, extracellular matrix secretion, and the like relating to formation of the bone cell may deteriorate.

Further, randomness of the voids is increased as an error range of the first intervals d1 is increased, which causes deterioration of interconnectivity and permeability between the voids. Regular voids having a small void error may promote regeneration of the bone as compared to irregular voids. In consideration of the first interval d1 in the range of 150 μm to 400 μm, the error range within ±20 μm may be considered as a uniform interval, and according to a method of manufacturing the scaffold 100 as will be described later, the error within ±20 μm may be assured.

In the second layer 20 coming into contact with soft tissue, the second interval d2 between the second fibers 22 may be in a range of 30 μm to 50 μm. This interval is a size that makes permeation of soft tissue difficult, and when this range is satisfied, soft tissue coming into contact with the second layer 20 may be prevented from permeating the damaged portion of bone tissue coming into contact with the first layer 10. In this case, the second intervals d2 existing in the second layer 20 may have an error within ±10 μm.

Specifically, it is known that the size of the void of a structure where permeation of soft tissue is impossible is 50 μm or less. Accordingly, the second interval d2 of the second fibers 22 should be 50 μm or less. On the other hand, if the second interval d2 is less than 30 μm, a chance of transmission of nutrients and oxygen is blocked, which is not preferable. Accordingly, the range of 30 μm to 50 μm may be an optimum range at which oxygen and nutrients can be basically transmitted and permeation of soft tissue can be prevented. Further, considering that the second interval d2 is in the range of 30 μm to 50 μm, the error range within ±10 μm may be a uniform interval.

As described above, in the scaffold 100 of the first exemplary embodiment, the size of the void of the first layer 10 coming into contact with bone tissue, that is, the first interval d1 is set to a size optimized to regenerate bone tissue, and the size of the void of the second layer 20 coming into contact with soft tissue, that is, the second interval d2 is set to a size optimized to prevent permeation of soft tissue, and thus the first interval and the second interval are differently set.

If the first interval d1 and the second interval d2 are identically set, a chance of permeation of soft tissue is reduced, but since fusing between bone tissue and the scaffold is not performed well, the scaffold is stripped, and thus a possibility of exposure thereof is increased. This leads failure of a scaffold operation.

In addition, if the second interval d2 and the first interval d1 are identically set, since soft tissue passes through the second layer 20 and the first layer 10 to easily permeate the damaged portion of bone tissue, bone tissue is guided, and thus a space where regeneration is to be performed is reduced. That is, since a chance of regeneration of the damaged portion of the bone into the bone is reduced, a role of the scaffold, which is guided bone regeneration, cannot be performed well.

However, in the scaffold 100 of the first exemplary embodiment, the size of the void corresponding to characteristics of the first layer 10 and the second layer 20 may be set to smoothly fuse bone tissue and the scaffold 100 and prevent soft tissue from permeating the damaged portion of bone tissue. Accordingly, the scaffold 100 of the first exemplary embodiment may prevent failure of the operation according to stripping and exposure and smoothly perform a guided bone regeneration function.

Further, in the scaffold 100 of the first exemplary embodiment, the first layer 10 is manufactured into a biopolymer having excellent affinity with bone tissue, and the second layer 20 is manufactured into a biopolymer having excellent affinity with soft tissue.

Specifically, the second layer 20 coming into contact with soft tissue includes polycaprolactone (PCL) that is a biopolymer having mechanical strength suitable for soft tissue and excellent elastic force.

On the other hand, the second layer 20 includes polycaprolactone (PCL) as a main component, and may include at least one of polylactic acid (PLA), polyglycolic acid (PGA), and polylactic-co-glycolic acid (PLGA) as an accessory component in addition to polycaprolactone (PCL).

Hydrophilicity is an important factor in adhesion and proliferation of the cell, and the polylactic acid (PLA), the polyglycolic acid (PGA), and the polylactic-co-glycolic acid (PLGA) have hydrophilicity that is higher than that of polycaprolactone (PCL) and thus may supplement hydrophilicity of polycaprolactone (PCL). In addition, since a biodegradable speed of the second layer 20 including the aforementioned accessory component may be higher than that of the case of only polycaprolactone (PCL), there is a further advantage in regeneration of bone tissue. Further, the polylactic acid (PLA), the polyglycolic acid (PGA), and the polylactic-co-glycolic acid (PLGA) have mechanical elastic force and hardness that are higher than those of polycaprolactone (PCL) and thus serve to reinforce mechanical property values of polycaprolactone (PCL).

The first layer 10 coming into contact with bone tissue is formed of a mixture of the biopolymer constituting the second layer 20 and an inorganic material that can maximize guiding of bone tissue regeneration, that is, a bone constituent component ceramic. The bone constituent component ceramic may be hydroxyapatite or tricalcium phosphate (TCP).

The first layer 10 may be formed of a material where at least one of hydroxyapatite and tricalcium phosphate (TCP) is mixed with polycaprolactone (PCL). On the other hand, the first layer 10 may be formed of a material where polycaprolactone (PCL) as the main component, at least one of the polylactic acid (PLA), the polyglycolic acid (PGA), and the polylactic-co-glycolic acid (PLGA) as the accessory component, and at least one of hydroxyapatite and tricalcium phosphate are mixed.

The scaffold 100 made of the biopolymer has bioaffinity that is better than that of a non-water absorbent material such as ePTFE (expanded polytetrafluoroethylene) or titanium. Further, the fibers 11 and 22 having predetermined thicknesses are regularly arranged with directionality and thus have excellent mechanical strength, and since a fiber length is sufficiently long as compared to a fiber width, elastic force and flexibility are excellent.

Further, in the scaffold 100 of the first exemplary embodiment, the bone constituent component ceramic is mixed with the biopolymer to form the first layer 10, and thus bone tissue regeneration may be effectively guided, mechanical strength of the first layer 10 may be increased, and surface roughness of the first layer 10 may be increased to increase an adhesion effect with bone tissue.

Further, heights of the first layer 10 and the second layer 20 may each be in the range of 50 μm to 100 μm. In FIG. 2, the height of the first layer 10 is represented by h1, and the height of the second layer 20 is represented by h2. h1 is the same as a thickness or a diameter of the first fiber 11, and h2 is the same as a thickness or a diameter of the second fiber 22.

The scaffold 100 of the first exemplary embodiment is manufactured by a procedure of spraying a first fiber material and a second fiber material in a molten state from a nozzle and laminating the materials. The fiber material in the molten state sprayed from the nozzle is hardened within several seconds to be solidified, and in this case, the heights h1 and h2 of the layers 10 and 20 are each closely related with adherence between the layers.

If the height h1 and h2 of the first layer 10 and the second layer 20 are each less than 50 μm, there is difficulty in actual processing and stable lamination, and if the height is more than 100 μm, since adherence between the layers is not sufficient, when the scaffold 100 is bent, a stripping phenomenon between the layers may occur. The stripping phenomenon between the layers is a serious problem causing failure of clinical application.

Figure 4A:
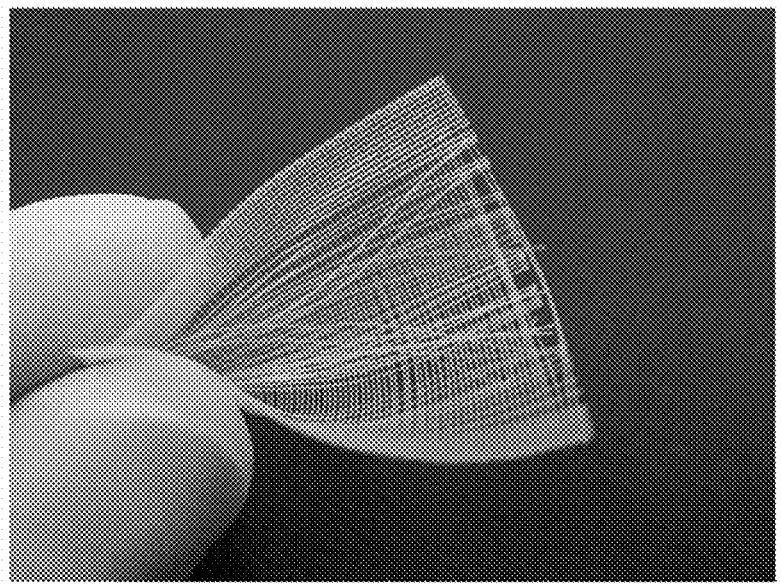
FIG. 4A is a scaffold picture according to a Comparative Example in which a first layer and a second layer are each formed to have a height of 120 μm.
Figure 4B:
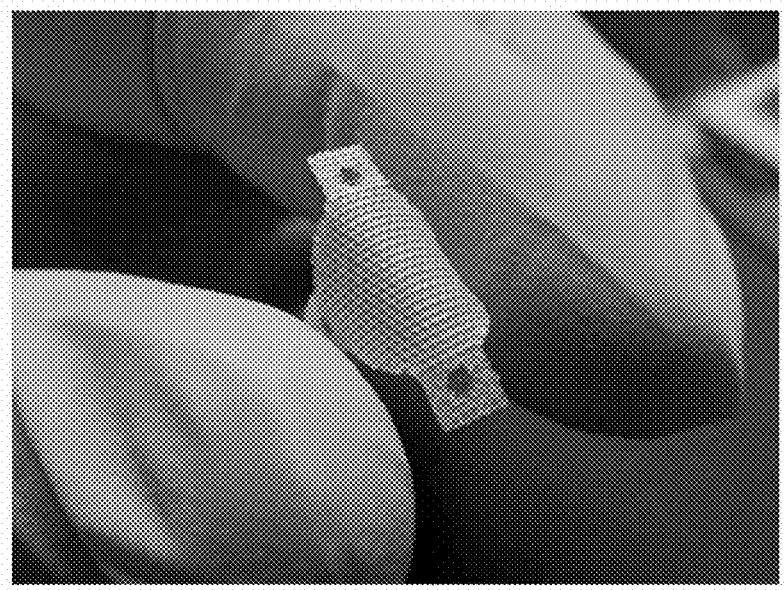
FIG. 4B is a scaffold picture according to an exemplary embodiment in which a first layer and a second layer are each formed to have a height of 60 μm.

FIG. 4A is a scaffold picture according to a Comparative Example in which a first layer and a second layer are each formed to have a height of 120 μm, and FIG. 4B is a scaffold picture according to an exemplary embodiment in which a first layer and a second layer are each formed to have a height of 60 μm.

It can be confirmed that in the scaffold of FIG. 4A, the first layer and the second layer are separated and thus the scaffold is stripped. On the other hand, it can be confirmed that in the scaffold of FIG. 4B, a stable adhesion state is exhibited without a stripping phenomenon.

Figure 5:
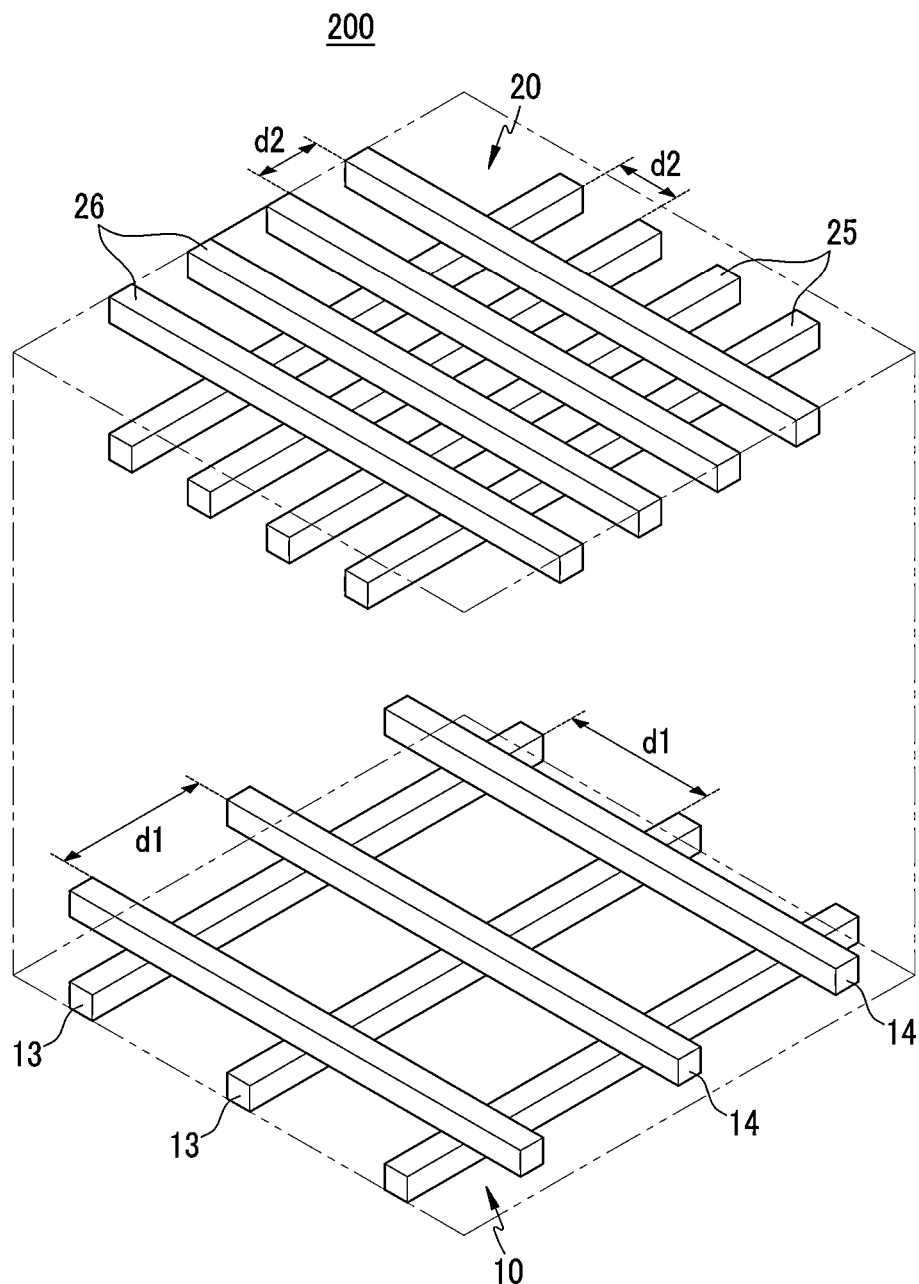
FIG. 5 is a schematic perspective view of a membrane type scaffold according to a second exemplary embodiment of the present invention.

FIG. 5 is a schematic perspective view of a membrane type scaffold (hereinafter, referred to as 'scaffold') according to a second exemplary embodiment of the present invention.

Referring to FIG. 5, in a scaffold 200 of the second exemplary embodiment, a first layer 10 coming into contact with bone tissue and a second layer 20 coming into contact with soft tissue are constituted by a plurality of fiber layers.

Specifically, the first layer 10 includes third fibers 13 arranged in parallel at first intervals d1 and extending in a third direction, and fourth fibers 14 arranged in parallel at the first intervals d1 and extending in a fourth direction crossing the third direction. The fourth fibers 14 are fixed onto the third fibers 13, and the first layer 10 is formed of a structure where the fiber layer of the third fibers 13 and the fiber layer of the fourth fibers 14 are laminated.

The third direction and the fourth direction may or may not be orthogonal to each other. Further, the third fibers 13 and the fourth fibers 14 may have various cross-sectional shapes such as a quadrangle, a circle, and an oval. FIG. 4 illustrates the case where the third fibers 13 and the fourth fibers 14 having the quadrangular cross-sectional shape are orthogonal to each other as an example, but the crossing angle and the cross-sectional shape of the third fibers 13 and the fourth fibers 14 are not limited to the illustrated example.

The first interval d1 has a size advantageous to bone tissue regeneration, that is, the range of 150 μm to 400 μm, and the first intervals d1 existing in the first layer 10 may have an error within ±20 μm. Further, the third fibers 13 and the fourth fibers 14 are made of the same material as the first fibers 11 described in the first exemplary embodiment and thus exhibit high affinity with bone tissue.

The second layer 20 includes fifth fibers 25 arranged in parallel at second intervals d2 and extending in a fifth direction, and sixth fibers 26 arranged in parallel at the second intervals d2 and extending in a sixth direction crossing the fifth direction. The sixth fibers 26 are fixed onto the fifth fibers 25, and the second layer 20 is formed of a structure where the fiber layer of the fifth fibers 25 and the fiber layer of the sixth fibers 26 are laminated.

The fifth direction and the sixth direction may or may not be orthogonal to each other. The fifth fibers 25 and the sixth fibers 26 may have various cross-sectional shapes such as a quadrangle, a circle, and an oval. FIG. 4 illustrates the case where the fifth fibers 25 and the sixth fibers 26 having the quadrangular cross-sectional shape are orthogonal to each other as an example, but the crossing angle and the cross-sectional shape of the fifth fibers 25 and the sixth fibers 26 are not limited to the illustrated example.

The second interval d2 has a size where permeation of soft tissue is difficult, that is, the range of 30 μm to 50 μm, and the second intervals d2 existing in the second layer 20 may have an error within ±10 μm. Further, the fifth fibers 25 and the sixth fibers 26 are made of the same material as the second fibers 22 described in the first exemplary embodiment and thus exhibit high affinity with soft tissue.

The height of each of the third fibers 13 and the fourth fibers 14 of the first layer 10 and the fifth fibers 25 and the sixth fibers 26 of the second layer 20 may be in a range of 50 μm to 100 μm. When this range is satisfied, high adherence may be implemented to suppress a stripping phenomenon between the layers.

On the other hand, in the above, the case where all of the first layer 10 and the second layer 20 are constituted by the plurality of fiber layers is described, but any one of the first layer 10 and the second layer 20 may be constituted by a short fiber layer and the other may be constituted by the plurality of fiber layers.

Figure 6:
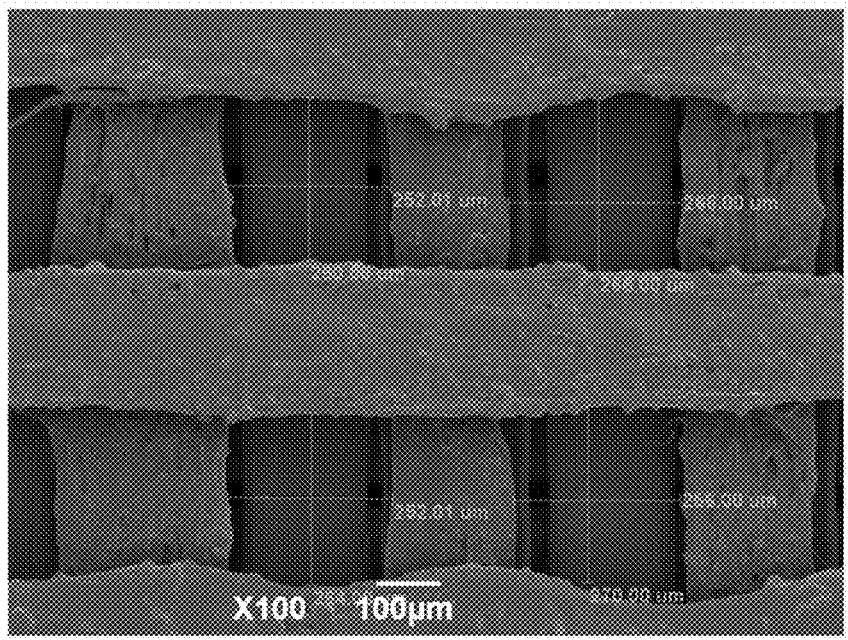
FIG. 6 is a scanning electron microscope (SEM) picture illustrating a first layer in the scaffold according to the second exemplary embodiment of the present invention.
Figure 7:
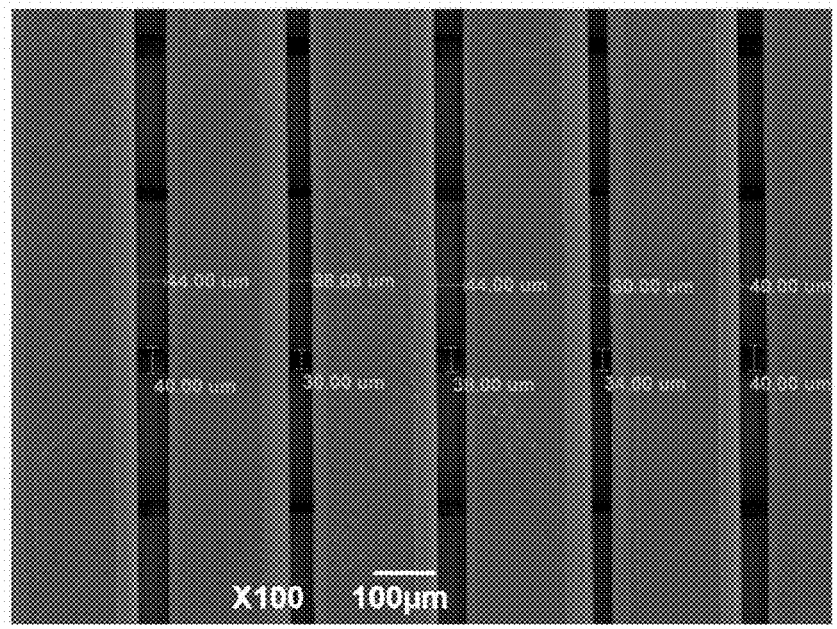
FIG. 7 is a scanning electron microscope (SEM) picture illustrating a second layer in the scaffold according to the second exemplary embodiment of the present invention.

FIG. 6 is a scanning electron microscope (SEM) picture illustrating the first layer in the scaffold according to the second exemplary embodiment, and FIG. 7 is a scanning electron microscope (SEM) picture illustrating the second layer in the scaffold according to the second exemplary embodiment.

Referring to FIG. 6, the third fibers and the fourth fibers of the first layer coming into contact with bone tissue are at the intervals of 250±20 μm, and are formed of a mixture of polycaprolactone (PCL), polylactic-co-glycolic acid (PLGA), and tricalcium phosphate (TCP). The third fibers and the fourth fibers have a rough surface by the mixing of tricalcium phosphate (TCP), and there is an effect that the rough surface makes fusing with peripheral bone tissue smooth.

Referring to FIG. 7, the fifth fibers and the sixth fibers of the second layer coming into contact with soft tissue are at the intervals of 35±10 μm, and are formed of a mixture of polycaprolactone (PCL) and the polylactic-co-glycolic acid (PLGA). The second layer does not include tricalcium phosphate (TCP) and thus has a smooth surface, which is effective to prevent inflowing of soft tissue.

Figure 8:
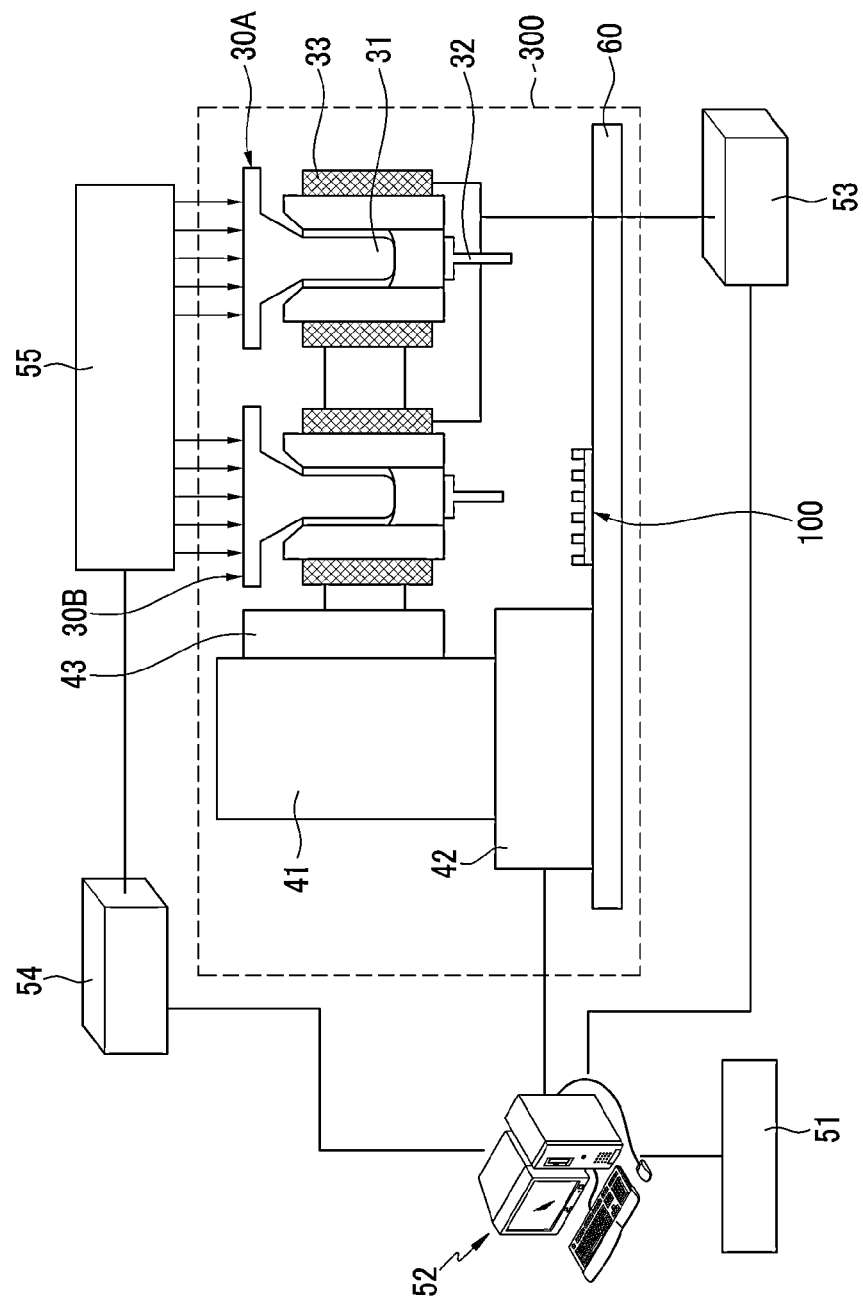
FIG. 8 is a schematic diagram illustrating a constitution of a multi-head deposition system for manufacturing the scaffold.

FIG. 8 is a schematic diagram illustrating a constitution of a multi-head deposition system for manufacturing the scaffold. The multi-head deposition system is used in order to manufacture the scaffold of the present exemplary embodiment.

A solid free-from fabrication mode is a technology of manufacturing a desired three dimensional form by converting free form information obtained from CAD data based on a rapid prototype technology into a G-code to deposit materials layer by layer. The multi-head deposition system is a system of manufacturing a scaffold for three dimensional tissue engineering by applying the solid free-from fabrication mode.

The multi-head deposition system is a system where a position, a temperature, and a pressure can be each independently controlled, and the three dimensional scaffold is manufactured in a mode of melting the material in a thermal melting mode and then pneumatically spraying the molten material.

Referring to FIG. 8, a multi-head deposition system 300 includes a first deposition head 30A and a second deposition head 30B spouting the scaffold material in a predetermined width. Each of the deposition heads 30A and 30B includes a syringe 31 where the material flows thereinto and the material is stored, a nozzle 32 spraying the material flowing into the syringe 31, and a heater 33 appropriately maintaining a temperature of the material.

In the present exemplary embodiment, a scaffold 100 is formed by providing a first biopolymer (biopolymer for manufacturing the first layer) to the syringe 31 of the first deposition head 30A, providing a second biopolymer (biopolymer for manufacturing the second layer) to the syringe 31 of the second deposition head 30B, and spraying the biopolymer through each nozzle 32. The first biopolymer and the second biopolymer are provided in a solid state to the syringe 31, and then heated by the heater 33 to be maintained in a molten state suitable for spraying.

The multi-head deposition system 300 includes an x-axis displacement moving portion 41 moving the first and second deposition heads 30A and 30B in an x-axis direction, an y-axis displacement moving portion 42 moving the first and second deposition heads 30A and 30B in an y-axis direction, and a z-axis displacement moving portion 43 moving the first and second deposition heads 30A and 30B in a z-axis direction.

The shape of the scaffold 100 to be manufactured is inputted through a data model 51 to an integrated control device 52, and the integrated control device 52 controls an operation of the multi-head deposition system 300 according to a three dimensional form data model of the scaffold 100. Accordingly, the multi-head deposition system 300 sprays the material of the scaffold 100 while moving the first and second deposition heads 30A and 30B to coordinate values to be set according to the three dimensional form data of the scaffold 100 transmitted from the integrated control device 52.

A temperature controller 53 is connected to the first and second deposition heads 30A and 30B to control a temperature of the syringe 31. The temperature controller 53 is connected to the heater 33 attached to the first and second deposition heads 30A and 30B to control the heater, and thereby heats or maintains the biopolymer in the syringe 31 to or at a predetermined temperature. Accordingly, the biopolymer may be changed or maintained into or in a state suitable for spraying to be sprayed through the nozzle 32 in a predetermined thickness.

A pressure controller 54 is connected to the first and second deposition heads 30A and 30B to control pressure transmitted to the first and second deposition heads 30A and 30B and adjust a spray speed of the biopolymer sprayed through the nozzle 32. The pressure controller 54 may be a pneumatic type, and may be provided with a pneumatic device 55 directly applying the pressure to the first and second deposition heads 30A and 30B. The pneumatic device 55 may be independently connected to each head of the multi-head deposition system 300 to variously adjust pneumatic pressure for each head.

Next, a method of manufacturing the scaffold 100 by using the aforementioned multi-head deposition system 300 will be described.

Figure 9A:
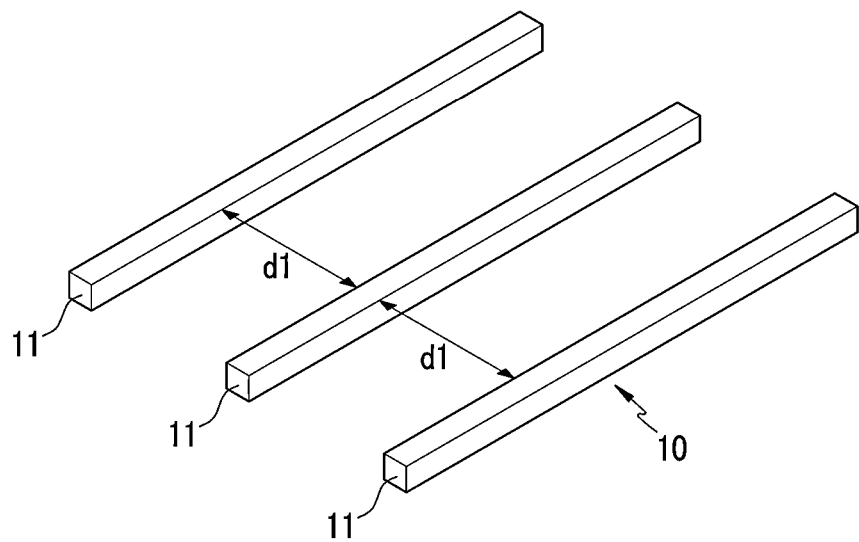
FIGS. 9A and 9B are schematic diagrams sequentially illustrating a procedure of manufacturing the scaffold by using the multi-head deposition system illustrated in FIG. 8.
Figure 9B:
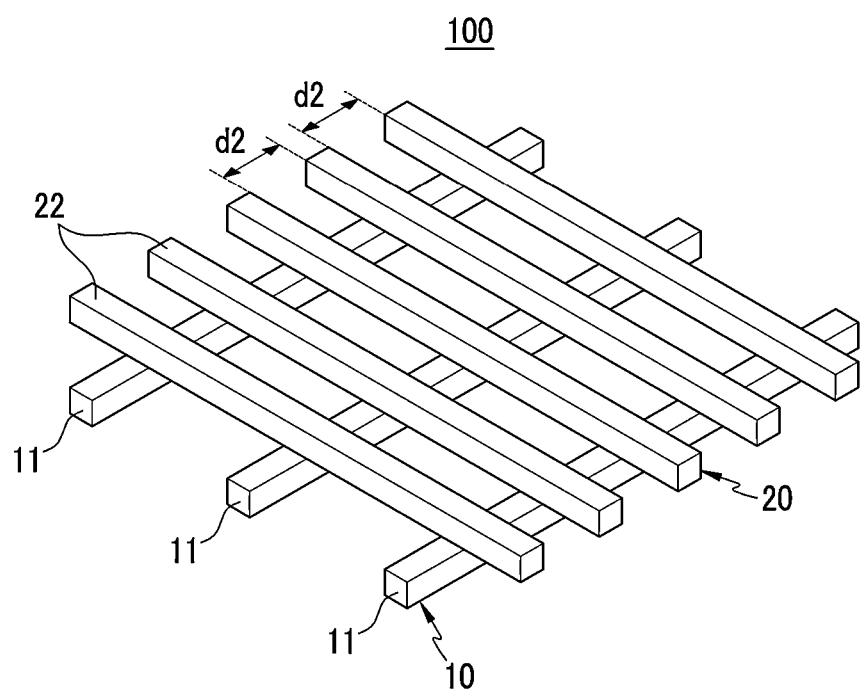

FIGS. 9A and 9B are schematic diagrams sequentially illustrating a procedure of manufacturing the scaffold by using the multi-head deposition system illustrated in FIG. 8.

Referring to FIGS. 8, 9A, and 9B, the scaffold 100 is designed by using a CAD program. Form information of the designed scaffold 100 is transmitted from the data model 51 to the integrated control device 52. The integrated control device 52 controls the temperature controller 53, the pressure controller 54, and the displacement moving portions 41, 42, and 43 based on transmitted form information.

The first biopolymer is provided to the syringe 31 of the first deposition head 30A, and the second biopolymer is provided to the syringe 31 of the second deposition head 30B. In addition, the first and second biopolymers are heated to the temperature suitable to be sprayed by using the temperature controller 53 and the heater 33.

Subsequently, the first deposition head 30A receives controlling of the displacement moving portions 41, 42, and 43 and the pressure controller 54, and sprays the first biopolymer through the nozzle 32 on a work table 60 to form the first layer 10 formed of the first fibers 11 (refer to FIG. 9A). On the other hand, the first layer including the third fibers and the fourth fibers crossing each other may be formed by spraying the first biopolymer.

In addition, the second deposition head 30B receives controlling of the displacement moving portions 41, 42, and 43 and the pressure controller 54, and sprays the second biopolymer through the nozzle 32 on the first layer 10 to form the second layer 20 formed of the second fibers 22 (refer to FIG. 9B). On the other hand, the second layer including the fifth fibers and the sixth fibers crossing each other may be formed by spraying the second biopolymer.

As described above, the scaffold 100 where the first fibers 11 arranged at the first intervals d1 and the second fibers 22 arranged at the second intervals d2 are laminated and cross each other may be formed by using the multi-head deposition system 300.

According to this manufacturing method, since toxic organic solvents are not used in a manufacturing procedure, the cell-affinitive scaffold 100 may be manufactured. Further, the width, interval, and height of the fibers constituting the scaffold 100 may be easily adjusted by adjusting the temperature, the pressure, and the nozzle transporting speed, and thus the scaffold 100 having various shapes may be easily manufactured.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims, detailed description of the invention, and drawings.

The invention claimed is:

1. A membrane type scaffold comprising:
   a first layer configured to be disposed to come into contact with bone tissue in a body and including first fibers arranged in parallel at first intervals and extending in a first direction; and
   a second layer laminated on the first layer, configured to be disposed to come into contact with soft tissue in the body, and including second fibers arranged in parallel at second intervals and extending in a second direction crossing the first direction,
   wherein the first interval is larger than the second interval,
   wherein the first intervals are in a range of 150 µm to 400 µm, and the second intervals are in a range of 30 µm to 50 µm, and
   wherein the first intervals are uniform with an error range within ±20 µm, and the second intervals are uniform with an error range within ±10 µm.

2. The membrane type scaffold of claim 1, wherein:
   heights of the first fibers and the second fibers are each in a range of 50 µm to 100 µm.

3. The membrane type scaffold of claim 1, wherein:
the first fibers and the second fibers include polycaprolactone (PCL), and
the first fibers further include at least one of hydroxyapatite and tricalcium phosphate (TCP).

4. The membrane type scaffold of claim 3, wherein:
the first fibers and the second fibers further include at least one of polylactic acid (PLA), polyglycolic acid (PGA), and polylactic-co-glycolic acid (PLGA) as an accessory component in addition to polycaprolactone (PCL).

5. The membrane type scaffold of claim 1, wherein:
the first layer includes third fibers arranged at the first intervals and extending in a third direction, and fourth fibers fixed onto the third fibers, arranged at the first intervals, and extending in a fourth direction crossing the third direction, and
the second layer includes fifth fibers arranged at the second intervals and extending in a fifth direction, and sixth fibers fixed onto the fifth fibers, arranged at the second intervals, and extending in a sixth direction crossing the fifth direction.

6. The membrane type scaffold of claim 5, wherein:
heights of the third fibers, the fourth fibers, the fifth fibers, and the sixth fibers are each in a range of 50 μm to 100 μm.

7. The membrane type scaffold of claim 5, wherein:
the third fibers, the fourth fibers, the fifth fibers, and the sixth fibers include polycaprolactone (PCL), and
the third fibers and the fourth fibers further include at least one of hydroxyapatite and tricalcium phosphate (TCP).

8. The membrane type scaffold of claim 7, wherein:
the third fibers, the fourth fibers, the fifth fibers, and the sixth fibers further include at least one of polylactic acid (PLA), polyglycolic acid (PGA), and polylactic-co-glycolic acid (PLGA) as an accessory component in addition to polycaprolactone (PCL).

9. A method of manufacturing a membrane type scaffold, comprising:
providing a first biopolymer and a second biopolymer to syringes of a first deposition head and a second deposition head, respectively;
spraying the first biopolymer through a nozzle of the first deposition head to form a first layer including first fibers arranged in parallel at first intervals and extending in a first direction; and
spraying the second biopolymer through a nozzle of the second deposition head on the first layer to form a second layer including second fibers arranged in parallel at second intervals and extending in a second direction crossing the first direction,
wherein the first interval and the second interval have different values,
wherein the first layer is configured to be disposed to come into contact with bone tissue in a body, the second layer is configured to be disposed to come into contact with soft tissue in the body, and
wherein the first interval is larger than the second interval,
wherein the first intervals are in a range of 150 μm to 400 μm, and the second intervals are in a range of 30 μm to 50 μm, and
wherein the first intervals are uniform with an error range within ±20 μm, and the second intervals are uniform with an error range within ±10 μm.

10. The method of claim 9, wherein:
a height of at least one of the first layer and the second layer is in a range of 50 μm to 100 μm.

11. The method of claim 9, wherein:
the first layer and the second layer include polycaprolactone (PCL), and
the first layer further includes at least one of hydroxyapatite and tricalcium phosphate (TCP).

12. The method of claim 11, wherein:
the first layer and the second layer further include at least one of polylactic acid (PLA), polyglycolic acid (PGA), and polylactic-co-glycolic acid (PLGA) as an accessory component in addition to polycaprolactone (PCL).

* * * * *